United States Patent [19]

Tsuji et al.

[11] Patent Number: 5,798,244
[45] Date of Patent: Aug. 25, 1998

[54] SIAα 2,3GALβ 1,4GLCNAC α 2,8-SIALYLTRANSFERASE

[75] Inventors: Shuichi Tsuji; Yukiko Yoshida; Naoya Kojima; Nobuyuki Kurosawa; Toshiro Hamamoto, all of Saitama, Japan

[73] Assignee: The Institute of Physical and Chemical Research, Saitama, Japan

[21] Appl. No.: 626,994

[22] Filed: Apr. 3, 1996

[30] Foreign Application Priority Data

Apr. 3, 1995 [JP] Japan ......................... 7-77469

[51] Int. Cl.$^6$ .............................. C12N 9/10; C12N 15/54
[52] U.S. Cl. .............................. 435/193; 536/23.2
[58] Field of Search ........................... 435/193; 536/23.2

[56] References Cited

PUBLICATIONS

Varki, "Selectins and Other Mammalian Sialic Acid–binding Lectins", Current Opinion in Cell Biology, 4, pp. 257–266 (1992).

Hakomori, "Glycosphingolipids in Cellular Interaction, Differentiation, and Oncogenesis", Ann. Rev. Biochem., 50, pp. 733–764 (1981).

Fishman et al., "Biosynthesis and Function of Gangliosides", Science, 194, pp. 906–915 (Nov. 26, 1976).

Broquet et al., "Glycoprotein Sialyltransferases in Eucaryotic Cells", Int. J. Biochem., 23, pp. 385–389 (1991).

Weinstein et al., "Primary Structure of β–Galactoside α2,–6–Sialyltransferase" The Journal of Biological Chemistry, 262, pp. 17735–17743 (Dec. 25, 1987).

Sadler et al., "Purification of Homogeneity of β–Galactoside α2→3 Sialyltransferase and Partial Purification of an α–N–Acetylgalactosaminide α2→6 Sialyltransferase from Porcine Submaxillary Glands", The Journal of Biological Chemistry, 254, pp. 4434–4443 (Jun. 10, 1979).

Weinstein et al., "Purification of Galβ1→4GlcNAc α2→6 Sialyltransferase and a Gal(β1→3 (4) GlcNAc α2→3 Sialyltransferase to Homogeneity from Rat Liver", The Journal of Biological Chemistry, 257, pp. 13835–13844 Nov. 25, 1982).

Rearick et al., "Enzymatic Characterization of β–D–Galactoside α2→3 Sialyltransferase from Porcine Submaxillary Gland", The Journal of Biological Chemistry, 254, pp. 4444–4451 (Jun. 10, 1979).

Joziasse et al., "Purification and Enzymatic Characterization of CMP–sialic Acid: β–Galactosyl(1→3–N–Acetylgalactosaminide α2→3–Sialyltransferase" The Journal of Biological Chemistry 260, pp. 4941–4951.

Grundmann et al., "Complete cDNA Sequence Encoding Human β–Galactoside α–2,6–Sialyltransferase", Nucleic Acids Research, 18, p. 667 (1990).

Bast et al., "HB–6, CDw75, and CD76 Differentiation Antigens are Unique Cell–Surface Carbohydrate Determinants Generated by the β–Galactoside α2,6–Sialkyltransferase", The Journal of Cell Biology, 116, pp. 423–435 (Jan. 1992).

Hamamoto et al., "Two Step Single Primer Mediated Polymerase Chain Reaction: Application to Cloning of Putative Mouse, β–Galactoside α2,6–Sialyltransferase cDNA", Bioorganic & Medicinal Chemistry, 1, pp. 141–145 (1993).

Gillespie et al., "Cloning and Expression of the Galβ, 3GalNAc α2,3–Sialyltransferase", The Journal of Biological Chemistry, 267, pp. 21004–21010 (Oct. 15, 1992).

Lee et al., "Molecular Cloning and Expression of Galβ1, 3GalNAcα2,3–Sialyltransferase from Mouse Brain", Eur. J. Biochem., 216, pp. 377–385 (1993).

Wen et al., "Primary Structure of Galβ1,3(4)GlcNAc α2,3–Sialyltransferase Determined by Mass Spectrometry Sequence Analysis and Molecular Cloning", The Journal of Biological Chemistry, 267, pp. 21011–21019 (Oct. 15, 1992).

Kurosawa et al., "Molecular Cloning and Expression of GalNac α2,6–Sialyltransferase", The Journal of Biological Chemistry, 269, pp. 1402–1409 (Jan. 14, 1994).

Kurosawa et al., "Cloning and Expression of Galβ1, 3GalNAc–specific GalNAc α2,6–Sialyltransferase", The Journal of Biological Chemistry, 269, pp. 19048–19053 (Jul. 22, 1994).

Sasaki et al., "Expression Cloning of a Novel Galβ(1–3/1–4)GlcNAc α2,3–Sialyltransferase Using Lectin Resistance Selection", The Journal of Biological Chemistry, 268, pp. 22782–22787 (Oct. 25, 1993).

Lee et al., "Cloning and Expression of cDNA for a New Type of Galβ1,3GalNAc α2,3–Sialyltransferase", The Journal of Biological Chemistry, 269, pp. 10028–10033 (Apr. 1, 1994).

Troy, "Polysialylation: From Bacteria to Brains", Glycobiology, 2, pp. 5–23 (1992).

Edelman, "Cell Adhesion and the Molecular Processes of Morphogenesis", Ann. Rev. Biochem., 54, pp. 135–169 (1985).

Cunningham et al., "Neural Cell Adhesion Molecule: Structure, Immunoglobin–Like Domains, Cell Surface Modulation, and Alternative RNA Splicing", Science, 236, pp. 799–806 (May 15, 1987).

Rutishauser et al, "The Neural Cell Adhesion Molecular (NCAM) as a Regulator of Cell–Cell Interactions", Science, 240, pp. 53–57 (Apr. 1, 1988).

(List continued on next page.)

Primary Examiner—Rebecca E. Prouty
Attorney, Agent, or Firm—Greenblum & Bernstein, P.L.C.

[57] ABSTRACT

The subject invention provides Siaα2,3 Galβ1,4GlcNAcα2,8-sialyltransferase and an enzymatically active fragment thereof, and a nucleotide sequence encoding said sialyltransferase. The subject invention also provides an extracellularly releasable protein capable of catalyzing Siaα2,3Galβ1,4GlcNAcα2,8-sialyltransfer which comprises the enzymatically active fragment of the Siaα2,3Galβ1,4GlcNAcα2,8-sialyltransferase together with a signal peptide.

6 Claims, 4 Drawing Sheets

OTHER PUBLICATIONS

Zuber et al., Polysialic Acid is Associated with Sodium Channels and the Neural Cell Adhesion Molecular N–CAM in Adult Rat Brain, *The Journal of Biological Chemistry*, 267, pp. 9965–9971 (May 15, 1992).

Sasaki et al., "Expression Cloning of a $G_{M3}$-specific $\alpha$-2, $\beta$-Sialyltransferase ($G_{D3}$ Synthase)", *The Journal of Biological Chemistry*, 269, pp. 15950–15956 (Jun. 3, 1994).

Kojima et al., "Enzymatic Activity of a Developmentally Regulated Member of the Sialyltransferase Family (STX): Evidence for $\alpha$2.8–Sialyltransferase Activivty Toward N–Linked Oligosaccharides", *FEBS Family* (STX): Evidence for $\alpha$2.8–Sialyltransferase Activivty Toward N–Linked Oligosaccharides, *FEBS Letters*, 360, pp. 1–4 (1995)

Kojima et al., "A Developmentally Regulated Member of the Sialyltransferase Family (ST8Sia II, STX) is a Polysialic Acid Synthase", *FEBS Letters*, 373, pp. 119–122 (1995).

```
ST8Sia-II(STX)    MQ---LQFRSWMLAALTLLVVFLIFADISEIE---EEIGNSGGRGTIRSA
ST8Sia-III        MRNCKMARVASVLGLVMLSVALLILSLISYVSLKKENIFTTPKYASPGAP
ST8Sia-I          MSPCGRALHTSRGAMAMLARKF------------------PRTRLPVG
(GD3 synthase)

ST8Sia-II(STX)    VNSLHSKSNRAEVVINGSSPPAVADRSNESLKHNIQPASSKWRHNQTLSL
ST8Sia-III        RMYMFHAGFRSQFALKFLDQSFVP--ITNSLTHELQEKPSKWTFNRTAFL
ST8Sia-I          ASALCVVVLCWLYIFPVYRPP-----NEKEIVQGVLAQSTAWRTNQTSAS
(GD3 synthase)

ST8Sia-II(STX)    RIRKQILKFLDAEKDISVLKGTLKPGDIIHYIFDRDS-TMNVSQNLYELL
ST8Sia-III        HQRQEILQHVDVIKNFSLTKSSVRIGQLMHYDYSSHKMVFSISNNFRSLL
ST8Sia-I          LFRRQMEDCCDPAHLFAMTKMNSPMGKSLWYD-GELLYSFTIDNSTYSLF
(GD3 synthase)

ST8Sia-II(STX)    PRTSPLKNKHFQTCAIVGNSGVLLNSGCGQEIDTHSFVIRCNRAPVQ-EY
ST8Sia-III        PDVSPIMNKRYNVCAVVGNSGILTGSQCGQEIDKSDFVSRCNFAPTE-AF
ST8Sia-I          PQATPF-QLPLKKCAVVGNGGILKMSGCGRQIDEANFVMRCNLPPLSSEY
(GD3 synthase)

ST8Sia-II(STX)    ARDVGLKTDLVIMNPSVIQRAFEDLVNATWREKLLQRLHGLNGSILWIPA
ST8Sia-III        HKDVGRKTNLTEFNPSILEKYYNNLLTIQDRNNFFLSLKKLDGAILWIPA
ST8Sia-I          TRDVGSKTQLVTANPSIIRQRFENLLWS--RKKFVDNMKIYNHSYIYMPA
(GD3 synthase)

ST8Sia-II(STX)    FMARGGKERVEWVNALILKH--HVNVRTAYPSLRLLHAVRGYWLTNKVHI
ST8Sia III        FFFHISATVTRTLVDFFVEHRGQLKVQLAWPG-NIMQHVNRYWKNKHLSP
ST8Sia-I          FSMKTGTEPSLRVY-YTLKDVGANQTVL-FANPNFLRNIGKFWKSRGIHA
(GD3 synthase)

ST8Sia-II(STX)    KRPTTGLLMYTLATRFCNQIYLYGFWPFPLDQN-QNPVKYHYYDSLKYGY
ST8Sia-III        KRLSTGILMYTLASAICEEIHLYGFWPFGFDPNTREDLPYHYYDKKGTKF
ST8Sia-I          KRLSTGLFLVSAALGLCEEVSIYGSWPFSVNMQG-DPISHHYYDNV-LPF
(GD3 synthase)

ST8Sia-II(STX)    TSQ-ASPHTMPLEFKALKSLHEQGALKLTVGQCDGAT-----      375
ST8Sia-III        TTKWQESHQLPAEFQLLYRMHGEGLTKLTLSHC---A-----      380
ST8Sia-I          TG----YHAMPEEFLQLWYLHRIGALRMQLDPCEAPSPQPTS       355
(GD3 synthase)
```

SIAα 2,3GALβ 1,4GLCNAC α 2,8-SIALYLTRANSFERASE

FIELD OF THE INVENTION

The present invention relates to an enzyme catalyzing syntheses of saccharide chains and to DNAs encoding said enzyme. More specifically, the present invention relates to a novel α2,8-sialyltransferase (ST8SiaIII) having activities toward Sia α2,3Gal β,1,4GlcNAc sequences of N-linked oligosaccharides and glycolipids, and to DNAs encoding the enzyme. The enzyme is useful as a medicament having pharmacological activities such as prevention of cancerous metastasis, maturation of sperm, inhibition of inflammatory reactions, and re-activation of nervous tissues. The enzyme is also useful as an agent for introducing oligosialic acids such as di-, tri-, or tetra-sialic acid to glyco-proteins and glycolipids for increasing physiological activities.

BACKGROUND OF THE INVENTION

Sialic acids are responsible for important physiological actions such as intercellular transmissions, cytoplasmic interactions, and cellular adhesions. Existences of wide variety of different cell-surface sialic acids are known, and they are regulated in processes of generations, differenciations, and transformations of oncogenes. Sialic acids are ubiquitous in the oligosaccharide side chains of glycoconjugates of a wide variety of animals (Varki, A., Curr. Opin. Cell. Biol. 4, pp.257–266, 1992).

Sialic acids exist at the end of hydrocarbon groups of glycoproteins and glycolipids. Sialic acids are enzymatically introduced to these positions from CMP-Sia during post-translation processes. For example, three sequential types, i.e., Siaα2,6Gal, Siaα2,3Gal, and Siaα2,6GalNAc, commonly exist in glycoproteins (Hakomori, S., Ann. Rev. Biochem., 50, 733–764, 1981), and two sequential types, i.e. Siaα2,3Gal and Siaα2,8Sia, are frequently observed in ganglyosides (Fishman, P., and Brady, R. O., Science, 194, 906–915, 1976).

Enzymes responsible for the above-mentioned enzymatic introductions of sialic acids (i.e. sialyltransfers) are glycosyltransferases that are refered to as sialyltransferases. It has been found that at least twelve different sialyltransferases are required for preparations of all types of the sialyloligosaccharide structures so far known (Broquet, P. et al., Int. J. Biochem., 23, 385–389, 1991; and Weinstein, J. et al., J. Biol. Chem., 262, 17735–17743, 1987). Among then, five sialyltransferases were purified and each of the purified enzymes was found to exhibit high specificities to respective acceptor substrates (Sadler, J. et al., J. Bio. Chem., 254, 4434–4443, 1979; Weinstein, J. et al., J. Biol. Chem., 257, 13835–13844, 1982; Rearick, J. et al., J. Biol. Chem., 254, 4444–4451, 1979; and Joziasse, D.H. et al., J. Biol. Chem., 260, 4941–4951, 1985).

With regard to cDNAs encoding the aforementioned sialyltransferases, cDNAs encoding Galβ1,4GlcNAcα2,6-sialyltransferases (Galβ4GlcNAc-α6ST) were cloned from various tissues such as liver (Weinstein, J. et al., J. Biol. Chem., 262, 17735–17743, 1987; Grundmann U. et al., Nucleic Acids Res. 18, 667, 1990; Bast, B. et al., J. Cell. Biol., 116, 423–435, 1992; and Hamamoto, T. et al., Bioorg. and Medic. Chem., 1, 141–145, 1993). In addition, cDNAs encoding Galβ1,3GalNAcα2,3-sialyltransferases (Galβ3GalNAc-α3ST: Gillespie, W. et al., J. Biol. Chem., 267, 21004–21010, 1992; and Lee, Y. et al., Eur. J. Biochem, 216, 377–385, 1993), and a cDNA encoding Galβ1,3(4)GlcNAcα 2,3-sialyltransferase (Galβ3(4)GlcNAc-α3ST: Wen, D. X et al., J. Biol. Chem., 267, 21011–21019, 1992) were also cloned.

Furthermore, cDNAs encoding two different types of GalNAcα2,6-sialyltransferases (EC 2.4.99.3; GalNAc-α6ST) were cloned by the inventors of the present invention, and their soluble proteins were prepared (Kurosawa, N. et al., J. Biol. Chem., 269, pp.1402–1409, 1994; and Kurosawa, N. et al., J. Biol. Chem., 269, pp.19048–19053, 1994). Some other publications also relate to clonings of cDNAs encoding sialyltransferases (e.g. Sasaki, K. et al., J. Biol. Chem., 268, 22782–22787, 1993; and Lee, Y.-C., J. Biol. Chem., 269, 10028–10033, 1994).

Siaα2,8Sia-sequences are widely observed in various gangliosides such as GT1a, GD3, and b- and c-series of gangliosides, and are more specifically found in mammal glycoproteins (Troy, F. A., Glycobiology 2, pp.5–23, 1992). It has been reported that Sia α2,8Sia-sequences are associated with only two proteins, i.e. the neutral cell adhesion molecule (N-CAM: Edelman, G. M., Annu. Rev. Biochem. 54, pp.135–169, 1985; Cunningham, B. A. et al., Science, 236, pp.799–806, 1987; and Rutishauser, U. et al., Science, 240, pp.53–57, 1988) and the α subunit of the voltage-gated sodium channels in rat brain (Zuber, C., J. Biol. Chem., 267, pp.9965–9971, 1992).

Recently, the inventors of the present invention cloned an α2,8-sialyltransferase, i.e. GD3-synthase (ST8SiaI: Sasaki, K. et al., J. Biol. Chem., 269, pp.15950–15956, 1994), and reported that a developmentally regulated sialyltransferase (STX, ST8SiaII) have N-glycan α2,8-sialyltransfer activity and polysialic acid synthesizing activity (Kojima, N. et al., FEBS Lett., 360, pp.1–4, 1995, and FEBS Lett., 373, pp.119–122, 1995). However, only two cDNAs encoding α2,8-sialyltransferase have been cloned so far, and the substrate specificities of these cloned α2,8-sialyltransferases do not give a full explanation as to how all of the Known Siaα2,8-Sia sequences in mammal glycolipids and glycoproteins are synthesized.

SUMMARY OF THE INVENTION

An object of the present invention is to provide a novel type of α2,8-sialyltransferase. Other objects of the present invention are to provide the amino-acid sequence of the α2,8- sialyltransferase and a cDNA encoding the same. Further object of the present invention is to provide a extracellularly releasable protein comprising an enzymatically active domain of the α2,8- sialyltransferase, and a method for mass production of such protein.

The inventors of the present invention conducted various studies to achieve the foregoing objects, and as a result, they cloned the CDNA encoding the Siaα2,3Galβ1,4GlcNAcα2,8-sialyltransferase from the mouse brain. The present invention was achieved on the basis of the above findings.

The present invention thus provides novel Siaα2,3Galβ1,4GlcNAcα2,8-sialyltransferase, and as a preferred embodiment thereof, Siaα2,3Galβ1,4GlcNAcα2,8-sialyltransferase 03 characterized by the amino-acid sequence of SEQ. ID. No.1 disclosed in the sequence listing.

According to another aspect of the present invention, nucleic acid sequences encoding said Siaα2,3Galβ1,4GlcNAcα2,8-sialyltransferase are provided. As a preferred embodinent of the present invention, there is provided the Siaα2,3Galβ1,4GlcNAcα2,8-sialyltransferase gene characterized by from nucleotide No. 123 to 1214 of the nucleic acid sequence of SEQ. ID. NO. 2;disclosed in the sequence listing.

A recombinant vector containing said Siaα2,3Galβ1, 4GlcNAcα2,8-sialyltransferase gene, and as a preferred embodiment, plasmide λCR03 are provided. A microorganism transformed by at least one of said vectors is also provided.

According to further aspect of the present invention, a enzymatically active domain of the Siaα2,3Galβ1,4GlcNAc α2,8-sialyltransferase is provided. As a preferred embodiment, the peptide sequence characterized by from amino acid No.26 to No.364 of SEQ. ID. No.1 is provided. Also provided is a polypeptide comprising said enzymatically active domain of the Siaα2,3Galβ1,4GlcNAcα2,8-sialyltransferase.

According to yet another aspect of the present invention, there is provided an extracellularly releasable protein capable of catalyzing a Siaα2,3Galβ8 1,4GlcNAcα2,8-sialyltransfer which comprises the polypeptide comprising the enzymatically active domain of the Siaα2,3Galβ1, 4GlcNAcα2,8-sialyltransferase together with at least one signal peptide. As a preferred embodiment thereof, a soluble protein characterized by the amino acid sequence of SEQ. ID. No.3 is provided.

There are also privided a gene encoding said protein, and as a preferred embodiment thereof, the gene characterized by the nucleic acid sequence of from nucleotide No. 14 to 1030 of SEQ.ID NO. 4. Also provided are a recombinant vector containing said gene encoding the protein, a microorganism transformed by at least one of the recombinant vectors, and a method for preparing the extracellularly releasable protein comprising the steps of cultivating the transformant and recovering said protein from the culture.

BRIEF DESCRIPTION OF THE DRAWINGS

FIG. 1 depicts the nucleic acid sequence (SEQ. ID. No.2) encoding Siaα2,3Galβ1,4GlcNAcα2,8-sialyltransferase 03 (mouse ST8Sia-III) as a preferred example of the Siaα2, 3Galβ1,4GlcNAcα2,8-sialyltransferases of the present invention, and deduced amino acid sequence thereof. In the figure, the double underlined amino acids correspond to a putative transmembrane domain, and the asterisks indicate potential N-glycosylation sites (Asn-X-Ser/Thr). Sialyl motifs L and S are boxed by solid and dashed lines, respectively, and the positions of the PCR primers are indicated by arrows. The amino acids are shown by the one-letter symbol.

FIG. 2 shows the amino acid sequence of the α2,8-sialyltransferase 03 of the present invention as compared to those of mouse ST8SiaI and mouse ST8SiaII. In the figure, amino acids are indicated by one letter symbol and ST8Sia-III represents the Sia α2,3Galβ1,4GlcNAcα2,8-sialyltransferase 03 of the present invention. The amino acids shared with ST8Sia-III and other sialyltransferases are shaded and sialyl motifs L and S are underlined.

DETAILED DESCRIPTION

A. Preferred Embodiments

Figure 3:
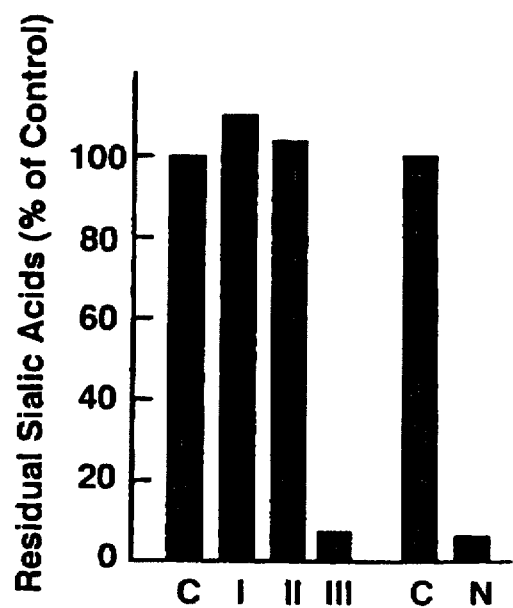
FIG. 3 shows the results of linkage analysis of sialic acids incorporated by the α2,8-sialyltransferase of the present invention. In the figure, C, I, II, III, and N represent treatment with no enzyme, NANase I, NANase II, NANase III, and N-glycanase, respectively.

As the most preferred example of the Siaα2,3Galβ1, 4GlcNAcα2,8-sialyltransferase of the present invention, Siaα2,3Galβ1,4GlcNAcα2,8-sialyltransferase 03 (SEQ. ID. No.1) is provided. The following descriptions detail the preparation and enzymatic characterizations of the α2,8-sialyltransferase 03. However, the Siaα2,3Galβ1, 4GlcNAcα2,8-sialyltransferase of the present invention is not limited to the α2,8-sialyltransferase 03, and thus the term "Siaα2,3Galβ1,4GlcNAcα2,8-sialyltransferase"as used herein means the polypeptide having the amino acid sequence set forth as SEQ. ID. No.1 as well as amino acid sequence variants thereof that are enzymatically active in Siaα2,3Galβ1,4GlcNAcα2,8-sialyltransfer. Examples of means for preparing such amino acid variants include, for example, substitution, insertion, and deletion of one or more amino acids.

The term "genes encoding the Siaα2,3Galβ1, 4GlcNAcα2,8- sialyltransferase" as herein means the nucleic acid sequence as set forth in SEQ. ID. No.2 and nucleic acid variants thereof, as well as DNAs encoding the amino-acid sequence of the above defined Siaα2,3Galβ1, 4GlcNAcα2,8-sialyltransferase including α2,8-sialyltransferase 03 and variants thereof. Examples of means for preparing such nucleic acid variants include, for example, substitution, insertion, and deletion of one or more nucleic acids. A detailed procedure for the cloning and expression of the gene encoding the Siaα2,3Galβ1, 4GlcNAcα2,8-sialyltransferase 03 (SEQ. ID. No.2), as a particularly preferred embodiment, will be set forth in the following Example. However, the descriptions are offerd by way of illustration only and are not intended to limit the present invention in any manner. It can readily be understood by an ordinary artisan that desired DNAs encoding α2,8- sialyltransferase of the present inveniton can be separated according to the experimental procedures disclosed in Example, together with appropriate modifications or alterations, if necessary.

Additionally, polypeptides comprising one or more enzymatically active domains derived from the Siaα2,3Galβ1, 4GlcNAcα2,8-sialyltransferase of the present invention fall within the scope of the present invention. The term "enzymatically active domain"as used herein means a polypeptide sequence which is derived from the above-defined Siaα2, 3Galβ1,4GlcNAcα2,8-sialyltransferase including the α2,8-sialyltransferase 03 and variants thereof and is enzymatically active in Siaα2,3Galβ1,4GlcNAcα2,8-sialyltransfer. An example of such enzymatically active domains is a part of the full polypeptide sequence of the α2,8-sialyltransferase 03 (SEQ. ID. No.1) which is characterized by the sequence of from amino acid No. 26 to 364 of SEQ. ID. No.1. Examples of the DNA encoding the enzymatically active domain include, for examle, the nucleic acid sequence encoding the polypeptide sequence characterized by the sequence of from amino acid No. 26 to 364 in SEQ. ID. No.1, and a preferred example thereof includes the nucleotide sequence characterized by from nucleic acid No. 198 to 1214 of SEQ. ID. NO.

It has been found that Siaα2,3Galβ1,4GlcNAcα2,8-sialyltransferase 03 stays inside host cells after its expression and remains unreleased extracellularly. In addition, the enzyme expressions may be decreased when endoplasmic concentration of the enzyme is above a certain threshold level. In order to efficiently utilize the Siaα2,3Galβ1, 4GlcNAcα2,8-sialyltransfer activity of the sialyltransferase of the present invention, soluble proteins can be prepared that retain the sialyltransfer enzymatic activity and are capable of being released from host cells after expression. An example of such soluble proteins includes, for example, an extracellularly releasable protein capable of catalyzing Siaα2,3Galβ1,4GlcNAcα2,8-sialyltransfer which comprises the enzymatically active domain derived from the Siaα2,3Galβ1,4GlcNAcα2,8-sialyltransferase of the present invention together with one or more signal peptides. The fused protein (SEQ. ID. No.3) comprising protein A and the enzymatically active domain of α2,8-sialyltransferase O3 is a particularly preferred example of the soluble protein.

The sialyltransferases so far cloned have domain structures similar to other glycosyltransferases, i.e. a short endoplasmic N-terminal tail; a hydrophobic signal anchor domain; a stem region having a protease sensitivity; and a large active domain at COOH-terminal (Paulson, J.C. and Colley, K.J., J. Biol. Chem., 264, 17615-17618, 1989). For the determination of a transmembrane region of the Siaα2,3Galβ1,4GlcNAcα2,8-sialyltransferase of the present invention, a hydrophobic index profile may be prepared and used according to the method of Kyte and Doolittle (Kyte, J. and Doolittle, R. F., J. Mol. Biol., 157, 105-132, 1982). For deducing the enzymatically active domains, recombinant plasmids introduced with various fragments can be prepared and used. Detailed procedures are described in the specification of PCT/JP94/2182 in reference to the determination of the transmembrane region and the deduction of the enzymatically active domains. However, applicable procedures are not limited to those disclosed procedures.

For the preparation of the extracellularly releasable protein, an immunoglobulin signal peptide sequence may be preferably used as the signal peptide, and the enzymatically active sequence derived from the α2,8-sialyltransferase of the present invention may preferably be subjected to an in-frame, fusion with said signal peptide. For example, the method of Jobling may be applied to the in-frame fusion (Jobling, S. A. and Gehrke, L., Nature(Lond.), 325, 622-625, 1987). Example set forth below details the preparation of the fused protein using protein A. However, types of the signal peptides and methods for preparing the soluble proteins are not limited to the disclosed procedures. It can readily understood by an ordinary artisan that the enzymatically active domain can be suitably chosen from the Siaα2,3Galβ1,4GlcNAcα2,8-sialyltransferase of the present invention, and that the extracellularly releasable proteins can easily be prepared by combining the active domain with one or more appropriate signal peptides according to known methods.

The enzyme of the present invention is characterized as a α2,8-sialyltransferase specific to Siaα2,3Galβ1,4GlcNAc sequence of N-linked oligosaccharides. The sialyltransferase of the present invention is thus useful as enzymatic agents for introducing a polysialic acid or an oligosialic acid such as di-, tri-, or tetra- sialic acid to proteins. The sialyltransferase of the present invention is also useful as medicaments for therapeutic treatments for hereditary diseases lacking enzymes for the biosynthesis of specified sugar chains. In addition, the sialyltransferase of the present invention is useful as medicaments for inhibition and prevention of cancerous metastasis or inflammatory reactions, or regeneration and re-activation of nervous tissues.

B. Examples

The gene encoding GD3 synthase (ST8Sia I) was cloned from human (Sasaki, K. et al., J. Biol. Chem. 269, pp.15950-15956, 1994; Nara, K. et al., Proc. Natl. Acad. Sci. U.S.A. 91, pp.7952-7956, 1994; Haraguchi, M. et al., Proc. Natl. Acad. Sci. U.S.A. 91, pp.10455-10459, 1994) and mouse. Recently, the inventors of the present invention identified the enzymatic activity of mouse STX (ST8Sia II) as that of an N-glycan α2,8-sialyltransferase and polysialic acid synthase (Kojima, N. et al., FEBS Lett., 360, pp.1-4, 1995, and FEBS Lett., 373, pp.119-122, 1995). To obtain the α2,8-sialyltransferase of the present invention that is characterized by properties distinguishable from the known α2,8-sialyltransferases, the inventors of the present invention conducted PCR cloning experiments using two degenerate oligonucleotide primers based on two highly conserved regions, sialyl motifs L and S, of human ST8Sia I (Sasaki, K. et al., J. Biol. Chem. 269, pp.15950-15956, 1994) and rat ST8Sia II (Livingston, B. D. et al., J. Biol. Chem., 268, pp.11504-11507, 1993).

PCR was performed using degenerate primers (5'-primer OP-L, T(G/A)(A/C)AGA(A/C)(A/T)TG(C/T)GC(G/C)(G/A)T(G/C)GTGGG(A/C)AA; 3'primer OP-S, CA(C/A)(A/T)G(A/G)GAAGGGCCAGAAGCCATA) deduced from conserved regions in STX (rat brain: Livingston, B. D. et al., J. Biol. Chem., 268, pp.11504-11507, 1993) and GD3 synthase (human melanoma cells: Sasaki, K. et al., J. Biol. Chem. 269, pp.15950-15956, 1994). Total RNA from 3-day-old mouse brain was used as a template to synthesize cDNA. The cycling parameters were 94° C. for 40 sec, 37° C. for 40 sec, and 72° C. for 1 min for the first 5 cycles, followed by 94° C. for 40 sec, 55° C. for 40 sec, and 72° C. for 1 min for 30 cycles.

The 0.5-Kb PCR. products were blunt-ended, kinated, and then subcloned into the SmaI site of pUC119. The subclones were characterized by sequencing. Approximately $10^6$ plaques of a 3-day-old mouse brain cDNA library (Lee, Y.-C. et al., J. Biol. Chem., 269, pp.10028-10033, 1994) were screened with the 0.5-kb-PCR fragments. Standard molecular cloning techniques, according to Maniatis et al., were used (Sambrook, J., Fritsch, E. F., and Maniatis, T., Molecular Cloning: a Laboratory Manual, 2nd edition, Cold Spring Harbor Laboratory, Cold Spring Harbor, N.Y., 1989).

Figure 1:
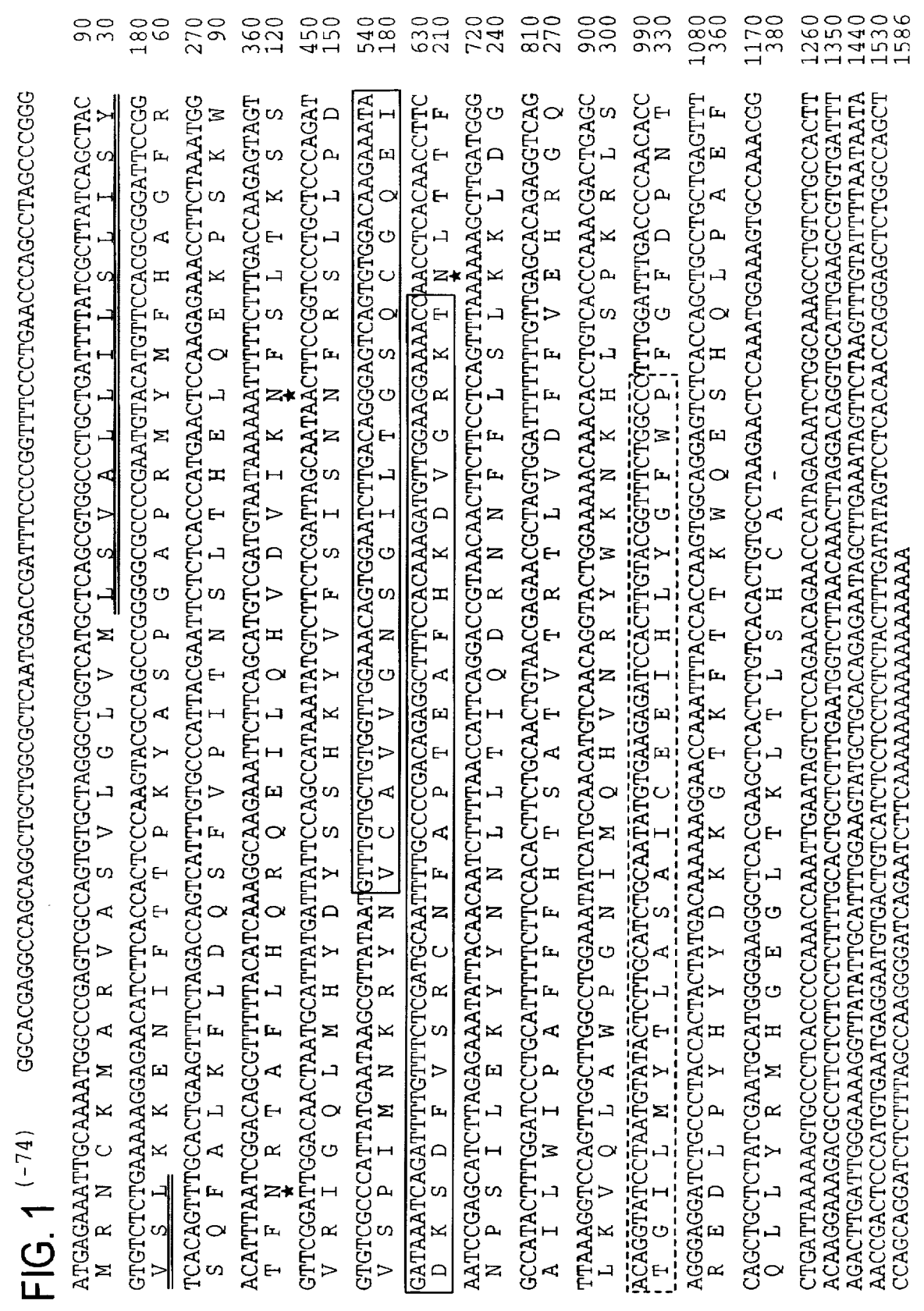

Among several clones, one clone, pCRO3, encoded a peptide exhibiting 35.6% and 41.9% identity to the 160-amino acid region of mouse ST8Sia I and mouse ST8Sia II, respectively. To isolate the complete coding sequence of the gene containing the 0.5-kb fragment, the mouse brain cDNA library was screened using the pCRO3 probe. Sequence analysis of the largest clone (1.7 kb; λCR03) revealed a continuous 380-amino acid open reading frame, including 74-bp of 5 'and 465-bp of a 3'non-coding region. FIG. 1 and SEQ. ID. No.2 depict the aforementioned DNA sequence of λCRO3, as a preferred example of the DNAs encoding Siaα2,3Galβ1,4GlcNAcα2,8-sialyltransferase of the present invention, and the amino acid sequence of Siaα2,3Galβ1,4GlcNAcα2,8-sialyltransferase (mouse ST8Sia-III) encoded by the nucleotide sequence.

In FIG. 1, the nucleotide and amino acid sequences are numbered from the presumed start codon and initiation methionine, respectively. The double underlined amino acids correspond to a putative transmembrane domain. The asterisks indicate potential N-glycosylation sites (Asn-X-Ser/Thr). Sialyl motifs L and S are boxed by solid and dashed lines, respectively. The positions of the PCR primers are indicated by arrows. The predicted amino acid sequence encoding a protein with a type II transmembrane domain, as found for so far cloned sialyltransferases, consisted of a NH₂-terminal cytoplasmic tail, a transmembrane domain, a proline-rich stem region, and a large COOH-terminal active domein.

Comparison of the amino acid sequence of the sialyltransferase of the present invention with other amino acid sequences in DNA and protein data banks did not reveal any similarity except with so far cloned sialyltransferases. On the other hand, some similarities were observed between the sialyltransferase of the present invention and other so far cloned sialyltransferases. The deduced amino acid sequence shows 27.6% and 34.4% identity to those of mouse ST8Sia I and mouse ST8Sia II, respectively (FIG. 2, wherein ST8Sia-III represents Siaα2,3Galβ1,4GlcNAcα2,8- sialyltransferase 03 of the present invention.). However, there is no significant similarity (10–15%) except for two stretches of sialyl motif L (45 residues: 165–205) and S (23 residues: 301–323) amino acids located in their active domains. Sialyl motif L shows 64–49% sequence identity, whereas sialyl motif S exhibits 61–22% identity to those of so far cloned sialyltransferases.

To facilitate functional analysis of the sialyltransferase of the present invention, expression plasmid pcDSA-03 was constructed and transfected into COS-7 cells, and the protein A fused-protein containing an active domain of the sialyltransferase of the present invention (i.e. a soluble enzyme; hereinafter referred to as the fused protein of the present invention) was adsorbed to IgG-Sepharose in the medium and used as the enzyme source. The amino acid sequence of the fused protein and the gene encoding the fused protein are shown as SEQ. ID. No.3 and 4, respectively.

A truncated form of the sialyltransferase of the present invention (ST8Sia-III), lacking the first 39 amino acids of the open reading frame, was prepared by PCR amplification with 5'- and 3'-primers containing a XhoI site, respectively (5'-CATCTTCTCGAGTCCC AAGTACGCCAGCCCG-3' and 5'-TTCCATCTCGAGTTCTTAGGCACAGTGTGACAG-3'). The amplified and digested 1028-bp XhoI fragment was inserted into the XhoI site of a pcDSA vector (Kojima, N. et al., FEBS Lett., 360, pp.1–4, 1995).

The single insertion in the correct orientation was finally analyzed by restriction enzyme treatment and DNA sequencing. The resulting plasmid was designated as pcDSA-03, which consisted of the IgM signal peptide sequence, a protein A IgG binding domain, and a truncated form of STBSia-III. COS-7 cells were transiently transfected with 10 μg of pcDSA-ST8Sia-III using the DEAE-dextran procedure and cultured according to the previously reported method (Kojima, N. et al., FEBS Lett., 360, pp.1–4, 1995). After 48 hr transfection, the culture medium was collected and the protein A-mouse STX expressed in the medium was adsorbed to IgG-Sepharose (15 μl of resin per 10 ml of culture medium) at 4° C. for 16 hr. The resin was collected by centrifugation, washed three times with phosphate-buffered saline, suspended in 50 μl (final volume) of Dulbecco's modified Eagle medium without fetal bovine serum, and used as the soluble enzyme.

The enzyme assays of the fused protein of the present invention and product characterizations were performed as follows: the enzyme activity was measured according to the method reported by Sasaki et al. (Sasaki, K. et al., J. Biol. Chem. 269, pp.15950–15956, 1994) in the presence of 0.1 M sodium cacodylate buffer (pH 6.0), 10 mM MgCl$_2$, 2 mM CaCl$_2$, 0.5% Triton CF-54, 100 μM CMP-[$^{14}$C]NeuAc (0.25 μCi), 10μg acceptor substrate, and 2 μl enzyme preparation in a total volume of 10 μl. After 4 hr incubation at 37° C., the reaction was terminated by the addition of SDS-PAGE loading buffer (10 μl), and the incubation mixtures were directly subjected to SDS-PAGE for glycoprotein acceptors.

For glycolipid acceptors, the incubation mixtures were applied on a C-18 column (Sep-Pak Vac. 100 mg; Waters, Milford, Mass, U.S.A.) which was washed with water. The glycolipids were eluted from the column with methanol, dried, and then subjected to chromatography on an HPTLC plate (Merck, Germany) with a solvent system of chloroform, methanol, and 0.02% CaCl$_2$ (55:45:10) according to the aforementioned method (Sasaki, K. et al., J. Biol. Chem., 269, pp.15950–15956, 1994). Acceptor substrates were visualized by staining with Coomassie Brilliant Blue for glycoproteins or by the orcinol/H$_2$SO$_4$ method for glycolipids. The radioactive materials in glycoproteins or glycolipids were visualized with a BAS2000 radio image analyzer (Fuji Film, Japan), and the radioactivity incorporated into acceptor glycoproteins was counted.

For linkage analysis of sialic acids, fetuin sialylated with the enzyme was precipitated with 70% ethanol, washed three times with 70% ethanol, dissolved in water, and then digested with a linkage-specific recombinant sialidase, NANase I (specific for α2,3-linked sialic acids, 0.1 U/ml), NANase II (specific for α2,3- and α2,6-linked sialic acids, 0.5 U/ml), or NANase III (specific for α2,3-, α2,6-, and α2,8-linked sialic acids, 0.35 U/ml)(FACE, Glyko, Inc., Navato, Calif.) at 37° C. for 8 hr.

For preparation of de-sialylated or de-N-glycosylated fetuin, fetuin (100 μg) was digested with NANase I (0.1 U/ml), NANase II (0.5 U/ml), or NANase III (0.35 U/ml) in a total volume of 20μl for 24 hr at 37° C., or with N-glycanase (1.5 U; Genzyme, Cambridge, Mass.) in a total volume of 20 μl at 37° C. for 36 hr. After inactivation of the enzyme by boiling for 1 min, the resulting de sialylated or de-N-glycosylated glycoproteins were used as acceptors.

Various glycoproteins were incubated with the fused protein of the present invention (i.e. Siaα2,3Galβ1,4GlcNAcα2,8-sialyltransferase in the form of the protein A-fused soluble enzyme), and then the reaction mixtures were analyzed by SDS-PAGE. When fetuin was used as an acceptor, strong sialyltransferase activity was detected, as seen in the case of mouse ST8Sia II. No activity toward fetuin was observed in the culture medium from cells transfected with the vector alone. Sialylated glycoproteins such as α1-acid glycoprotein, ovomucoid, and transferrin served as acceptors. However, the fused protein did not exhibit activity toward asialoglycoproteins at all.

In addition, various glycolipids were incubated with the fused protein of the present invention, and the resulting glycolipids were analyzed by HPTLC with a solvent system of CHCl$_3$/CH$_3$/CH$_3$OH)0.2% CaCl$_2$(55:45:10). $^{14}$C-Sialic acid incorporation from CMP-[$^{14}$C]NeuAc was also observed when GM3 was used as an acceptor substrate, as seen in the case of GD3 synthase (ST8Sia I). The fused protein of the present invention exhibits low activity toward GD3. 2,3-SPG (Siaα2,3Galβ1,4GlcNAcβ1,4Galβ1,4Glcβ, 1,1Cer) served as the best acceptor substrate among the tested glycolipids for the fused protein of the present invention.

On the other hand, 2,6-SPG did not serve as an acceptor at all for the fused protein of the present invention. Other gangliosides, such as GM1, GD$_1$a, GD$_1$b, GT$_1$b, and GQ$_1$b, as well as neutral glycosphingolipids did not serve as acceptor substrates for the fused protein of the present invention. There was no sialyltransferase activity toward gangliosides, including 2,3-SPG, as well as neutral glycosphingolipids in the medium obtained from COS-7 cells transfected with the vector without the insert.

The product synthesized from GM3 by the fused protein of the present invention was comigrated with authentic GD3 on HPTLC with two different solvent systems. In addition, a $^{14}$C-sialylated ganglioside was eluted from DEAE-Sephadex at the position of disialylated gangliosides. The linkages of the incorporated sialic acids were also confirmed by digestion of $^{14}$C-sialylated fetuin with linkage-specific sialidases.

Fetuin was $^{14}$C-sialylated with the fused protein of the present invention, and then the $^{14}$C-sialylated glycoprotein (1,000 cpm) was digested with α2,3-specific sialidase (NANase I), α2,3- and α2,6-specific sialidase (NANase II), or α2,3-, α2,6-, and α2,8-specific sialidase (NANase III). $^{14}$C-sialylated fetuin was also digested with N-glycanase (1.5 U) at 37° C. for 36 hr. The resulting glycoproteins were subjected to SDS-PAGE, visualized with BAS2000 image analyzer, and the residual radioactivity at the position of enzyme-treated fetuin was quantified.

The incorporated $^{14}$C-sialic acids were completely resistant to treatment with α2,3-specific sialidase or α2,3- and α2,6-specific sialidase, but almost completely disappeared on treatment with α2,3-, α2,6-, and α2,8-specific sialidase. The results are shown in FIG. 3. In the figure, C, I, II, III, and N represent treatment with no enzyme, NANase I, NANase II, NANase III, and N-glycanase, respectively. It is apparent from these results that the sialic acids incorporated by the fused protein of the present invention were linked to terminal sialic acids through α2,8-linkages and Sia α2,8Sia sequences were synthesized by the fused protein of the present invention, and thus the cloned gene λCRO3 encoded a novel α2,8-sialyltransferase 03 (ST8Sia III).

In view of the fact that the fused protein of the present invention exhibits activities toward 2,3-SPG and GM3 but not toward 2,6-SPG, the activity of the sialyltransferase 03 of the present invention may be specific to the Siaα2,3Gal-sequence. This possibility was confirmed by measuring the activity toward de-sialylated fetuin. Fetuin was digested with NANase I, II, or III, and each of the resulting de-sialylated glycoproteins was incubated with the fused protein of the present invention and subjected to SDS-PAGE, and then the radioactivity incorporated into the de-sialylated glycoproteins was visualized and quantified with BAS2000 radio image analyzer.

Figure 4:
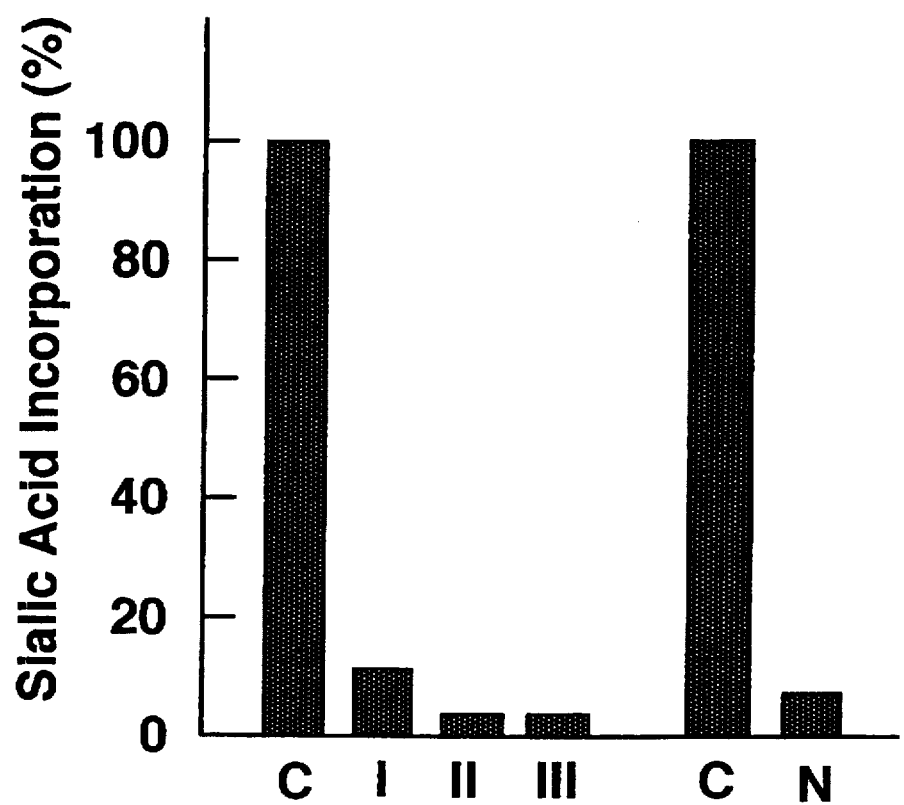
FIG. 4 shows the effects of treatment with sialidase and N-glycanase of fetuin on the activity of the α2,8-sialyltransferase of the present invention. In the figure, C, I, II, III, and N represent treatment with no enzyme, NANase I, NANase II, and NANase III, and N-glycanase, respectively.

The results are shown in FIG. 4. In the figure, C, I, II, and III represent treatment with no enzyme, NANase I, NANase II, and NANase III, respectively. Glycoproteins were first digested with N-glycanase. The resulting de-N-glycosylated glycoproteins were then incubated with the fused protein of the present invention and CMP-[$^{14}$C]NeuAc, and the incorporated sialic acids were visualized and counted. Symbols C and N represent treatments with no enzyme and N-glycanase, respectively.

The activity of the fused protein of the present invention toward de-sialylated fetuin on treatment with α2,3-specific sialidase, as well as that on treatment with α2,3- and α2,6-specific sialidase or α2,3-, α2,6-, and α2,8-specific sialidase, was completely abolished. Under the same digestion conditions, α2,3-SPG was desialylated by α2,3-specific sialidase, but 2,6-SPG was completely resistant toward treatment with a 2,3-specific sialidase.

To determine whether the sialic acids are incorporated into N-linked oligosaccharides or O-linked oligosaccharides of fetuin, $^{14}$C-sialylated fetuin was digested with N-glycanase. The sialic acids incorporated into fetuin were completely released from the proteins, and N-glycanase-treated fetuin did not serve as an acceptor (FIG. 4). Since GD$_{1}$a, GT$_{1}$b, GQ$_{1}$b, and O-linked oligosaccharides in fetuin, which contain Siaα2,3Galβ1,3GalNAc sequences, did not serve as acceptors for the fused protein of the present invention, and 2,3-SPG was a good acceptor for it, the activities of the fused protein are specific for the Sia α2,3Galβ1,4GalNAc sequences of N-linked oligosaccharides of glycoproteins as well as glycolipids.

TABLE 1

Comparison of the Acceptor Substrate Specificities of Three Cloned α 2,8-Sialyltransferases.

| Acceptors | ST8Sia III | ST8Sia II (STX) | ST8Sia (GD3 synthase) |
|---|---|---|---|
| | | (pmol/ml medium, h) | |
| (Glycoproteins) | | | |
| α1-Acid glycoprotein | 7.8 | 7.6 | 0[2] |
| Asialo-α1-acid glycoprotein | 0 | 0 | 0 |
| Fetuin | 92.1 | 8.0 | 0 |
| Asialofetuin | 0 | 0 | 0 |
| Ovomucoid | 1.7 | 1.3 | 0 |
| Transferrin (Bovine) | 1.3 | 0.38 | 0 |
| BSM | 0 | 0 | 0 |
| (Glycolipids) | | | |
| Lactosylceramide | 0 | 0 | 0 |
| GM3 | 2.1 | 0 | 0.18 |
| GD3 | 0.86 | 0 | 0 |
| GM1 | 0 | 0 | 0 |
| GD1a | 0 | 0 | 0 |
| GD1b | 0 | 0 | 0 |
| GT1b | 0 | 0 | 0 |
| GQ1b | 0 | 0 | 0 |
| 2,3-SPG | 7.5 | 0 | N.T.[3] |
| 2,6-SPG | 0 | 0 | N.T. |

[1] Human ST8SiaI (GD3 synthase) expressed by Namalwa cells was used (Sasaki, K. et al., J. Biol. Chem. 269, pp. 15950–15956, 1994).
[2] 0 indicates values under 0.1 pmol/ml medium, h for mouse ST8Sia II and III, and those under 0.01 pmol/ml medium, h for human ST8Sia I.
[3] N.T. indicates not tested.

The acceptor substrate specificity of the sialyltransferase of the present invention was compared to those of so far cloned α2,8-sialyltransferases, GD3 synthase (ST8Sia I) and STX (ST8Sia II), as shown in Table 1. STX exhibited sialyltranfer activity only toward sialylated glycoproteins such as α1-acid glycoproteins or fetuin, i.e. no activity being detected toward glycolipids including GM3 and 2,3-SPG, while GD3 synthase exhibited activity only toward GM3, but not toward sialylated glycoproteins. Comparison of the substrate specificities of these two α2,8-sialyltransferases revealed that the sialyltransferase of the present invention has rather broader activity.

Both sialylated glycoproteins and glycolipids served as acceptors for the sialyltransferase of the present invention. Although the substrate specificities for glycoproteins of the sialyltransferase of the present invention and ST8Sia II were similar to each other, fetuin acts as a better acceptor (10 fold) than α1-acid glycoprotein for the sialyltransferase of the present invention. For ST8Sia II, the incorporation of sialic acids into fetuin was almost the same as the sialic acid incorporation into α-acid glycoprotein. Thus, the structure of oligosaccharides on glycoproteins acting as acceptors for the sialyltransferase of the present invention is different from that in the case of ST8Sia II.

The substrate specificity of the sialyltransferase of the present invention toward glycolipids was rather similar to the substrate specificity of ST8Sia I (GD3 synthase), i.e. both sialyltransferases synthesized GD3 from GM3. However, the sialyltransferase of the present invention is characterized by the activity of synthesizing GT3 from GD3, which is not achieved by ST8Sia I. In addition, the sialyltransferase of the present invention has activity of introducing several units of sialic acid into the substrates.

The apparent Km values of the sialyltransferase of the present invention for 2,3-SPG, GM3, and GD3 were 68 μM 588 μC M. and 3,300 μM, respectively (Table 2). The Vmax/Km values set out in Table 2 clearly show that 2,3-SPG is a much more suitable acceptor for the sialyltransferase of the present invention as compared to GM3 or GD3. In addition, the Vmax/Km values for fetuin indicate that the sialyltransferase of the present invention has remarkably higher specificity toward complex-type N-linked oligosaccharides containing Siaα2,3Galβ1, 4GlcNAc sequence.

TABLE 2

Kinetic properties of the sialyltransferase of the present invention

| Acceptors | Km (mM) | Vmax (pmol/h, ml) | Vmax/Km |
|---|---|---|---|
| 2,3-SPG | 0.082 | 9.2 | 112.1 |
| GM3 | 0.588 | 3.7 | 6.3 |
| GD3 | 3.30 | 6.1 | 1.8 |
| Fetuin[1] | 0.020 | 424 | 21200 |

[1]The numbers of α 2,3-linked sialic cids on N-linked oligosaccharides (about 30 nmol/mg) were calculated from the difference between sialic acid residues in fetuin and those in a α 2,3-specific sialidase-treated fetuin, and the number of O-linked oligosaccharides (about 70 nmol/mg).

To evaluate the expression pattern and message size of the cloned gene that encodes the sialyltransferase of the present invention, total RNAs were isolated from several mouse tissues: brain, heart, liver, lung, kidney, spleen, salivary gland, thymus, testis, and placenta. Each of RNAs (5 μg) prepared from various adult mouse tissues was subjected to Northern blot hybridization analysis using the 1205-bp XhoI fragment of the cloned cDNA of the sialyltransferase of the present invention as hybridization probe.

5 μg fractionated on a denaturing formaldehyde-agarose gel (1%) and then transferred onto a nylon membrane (Nytran, Schleicher & Schuell). The full-length of ST8Sia-III cDNA (1205-bp) was amplified by PCR using synthetic oligonucleotide primers (5'-AGGCTCGAGCTCTCAATGGACCGATT-3' and 5'-TTCCATCTCGAGTTCTTAGGCACAGTGTGACAG-3') from 3-day-old mouse brain cDNA. The full length mouse GD3 synthase and mouse STX fragments (Kojima, N. et al., FEBS Lett., 360, pp.1–4, 1995) were prepared by PCR amplification, subcloned and sequenced. These fragments were radiolabeled and used as probes.

Three RNA species of 6.7-, 2.2-, and 1.7-kb were expressed in brain. Strong expression of a 3.7-kb transcript was observed in testis, but not in brain. The distribution of these transcripts was similar to that in the case of STX (ST8Sia II). The inventors of the present invention reported that the expression of the STX (ST8Sia II) gene was detected in fetal and newborn mouse brain (Kojima, N. et al., FEBS Lett., 360, pp.1–4, 1995). In order to compare ST8Sia III gene with other α2,8-sialyltransferase genes as to transcription patterns during mouse brain development, total RNAs (5 μg each) prepared from the brains of 14 and 20 p.c. fetal, and 3-day-, 2-week-, and 8-week-old mice was analyzed by Northern blot hybridization. As probes, full length cDNAs for the sialyltransferase of the present invention, mouse ST8Sia II (STX), and mouse STSia I (GD3 synthase) were used.

The transcripts of the sialyltransferase of the present invention first appeared in 20 p.c. fetal brain and then decreased in successive development. On the other hand, a 6.0-kb transcript of ST8Sia II was detected in 14 p.c. fetal brain and then the level of the transcript increased up to the peak level of 20 p.c. fetal brain. After then, ST8Sia II message decreased to an almost undetectable level within 2 weeks after the birth. An approximately 9-kb transcript of ST8Sia I was also expressed in the brain throughout development, its level being highest in 20 p.c. fetal brain. These results suggest that each of the three enzyme genes is expressed differently during brain development.

It has been shown that poly-α2,8-sialosyl sialyltransferase activity is restricted to an early stege of development (McCoy, R. D. et al., J. Biol. Chem., 260, pp.12695–12699, 1985). A Golgi-enriched fraction from 20-day-old fetal rat brain contains poly α2,8-sialosyl sialyltransferase activity toward N-CAM in vitro. However, a membrane fraction isolated from adult rat brain contains lower sialyltransferase activity and no poly-α2,8-sialosyl sialyltransferase activity. From the results of chemical analysis (Finne, J., J. Biol. Chem., 257, pp.11966–11970, 1982) and overexpression of Galβ1,4GlcNAcα2,6-sialyltransferase during Xenopus embryogenesis (Livingston, B. D. et al., Glycobiology 1, pp.39–44, 1990), it was suggested that the polysialic acids are attached to Sia α2,3-Gal-residues of an N-linked oligosaccharides. The gene expression pattern and substrate specificity of the sialyltransferase of the present invention suggested that the present sialyltransferase is very closely involved in the initial step of sialic acid polymerization, i.e. biosynthesis of Siaα2,8Sia α2,3Gal of N-glycan.

ST8sia II (STX), which was highly regulated during development of the brain, also exhibits α2,8-sialyltransferase activity and polysialic acid synthase activity solely toward N-linked oligosaccharides of glycoproteins, and thus it was suggested that the enzyme is involved in polysialic acid chain biosynthesis (Kojima, N. et al., FEBS Lett., 360, pp.1–4, 1995, and FEBS Lett., 373, pp.119–122, 1995). The structures of N-linked oligosaccharides as acceptors for ST8Sia II (STX) and the sialyltransferase of the present invention are essentially distinct in vivo, even if they overlap in part, for the following reasons: 1) the sialyltransferase of the present invention but not ST8Sia II exhibited activity toward 2,3-SPG; 2) incorporation of sialic acids into fetuin was 10-fold greater than that into α1-acid glycoproteins in the case of the sialyltransferase of the present invention, whereas that into fetuin and α1-acid glycoproteins was almost the same in that of ST8Sia II.

Since 2,3- and 2,6-SPGs did not serve as acceptors for mouse ST8Sia II, ST8Sia II may require not only the NeuAc α2,3Galβ1,4GlcNAc sequence but also a more complex structure containing the NeuAc α2,3Galβ1,4GlcNAc sequence for α2,8-sialyltransfer. On the other hand, the minimum structural requirement for sialyltransfer by the sialyltransferase of the present invention is Siaα2,3Galβ1, 4GlcNAc-R.

The reason why two different types of α2,8-sialyltransferase with similar substrate specificities toward N-linked oligosaccharide exist in mouse brain is not clear at present. One possibility is that the glycoproteins which act as acceptor substrates for ST8Sia II (STX) and the sialyltransferase of the present invention are different. Indeed, at least two brain glycoproteins, i.e. N-CAM and the αsubunit of voltage-gated sodium channels, are known to be polysialylated (Edelman, G. M., Annu. Rev. Biochem. 54, pp.135–169, 1985; Cunningham, B. A. et al., Science, 236, pp.799–806, 1987 ; Rutishauser, U. et al., Science, 240, pp.53–57, 1988; Zuber, C., J. Biol. Chem., 267, pp.9965–9971, 1992). Thus, ST8Sia II and the sialyltransferase of the present invention are possibly involved in the biosynthesis of polysialic acid of N-CAM and the αsubunit of voltage-gated sodium channels, respectively.

Another possibility is that the two enzymes have almost the same substrate specificity in vivo, but are controlled through different regulation systems. The gene expression of ST8Sia II (STX) and that of the sialyltransferase of the present invention during brain development are distinguishable from each other. ST8Sia II appeared first in 14 p.c. fetal brain and then completely disappeared, at least in 2-week-old mouse brain. In contrast, the gene of the sialyltransferase of the present invention was not expressed in 14 p.c. fetal brain. However, its expression was observed in 20 p.c. fetal brain, and although the expression was decreased during development, the enzyme was still expressed in 2-week old mouse brain.

It has been reported that the expression of polysialic acids of N-CAM is developmentally regulated, i.e. the embryonic form with a high sialic acid content undergoes postnatal conversion to the adult form with a low sialic acid content, although the core structure of N-linked oligosaccharides attached to polysialic acid chains during brain development have not been fully studied (Zuber, C., J. Biol. Chem. 267, pp.9965–9971, 1992; Hoffman, S. et al., J. Biol. Chem. 257, pp.7720–7729, 1982; Edelman, G. M., Science, 219, 450–457, 1983). ST8Sia II and the sialyltransferase of the present invention may be responsible for the polysialic acid chain biosynthesis of the embryonic and postnatal forms of N-CAM, respectively.

In the experiments set out above, unless otherwise specifically mentioned, the materials used were essentially the same as those described in the following publications: Sasaki, K. et al., J. Biol. Chem. 269, pp.15950–15956, 1994; Kurosawa, N. et al., J. Biol. Chem., 269, pp.1402–1409, 1994; Lee, Y.-C. et al., J. Biol. Chem., 269, pp.10028–10033, 1994; and Kurosawa, N. et al., J. Biol. Chem., 269, pp.19048–19053, 1994.

Lactosylceramide, GM3, GD3, $GD_1a$, $GD_1b$, and $GT_1b$ were purchased from Sigma (St. Louis, MO, USA); and $GQ_1b$ and paragloboside were from IATRON (Tokyo, Japan). $\alpha 2,3$- and $\alpha 2,6$- sialylparaglobosides (SPGs) were gifts from Dr. Iwamori, Tokyo University. Glycoproteins (fetuin, asialofetuin, $\alpha 1$ acid glycoprotein, ovomucoid, transferrin, and bovine submaxillary mucin) were from Sigma. Asialo- $\alpha 1$-acid glycoprotein and asialoovomucoid were prepared by mild acid hydrolysis of glycoproteins (0.02N, HCl,80° C., 1 h). Protein A-sepharose was from Pharmacia.

What is claimed is:

1. Siaα2,3Galβ1,4GlcNAcα2,8-sialyltransferase having the amino acid sequence:

Met Leu Ser Val Ala Leu Leu Ile
Leu Ser Leu Ile Ser Tyr Val 15
Ser Leu Lys Lys Glu Asn Ile Phe
Thr Thr Pro Lys Tyr Ala Ser 30
Pro Gly Ala Pro Arg Met Tyr Met 45
Phe His Ala Gly Phe Arg Ser
Gln Phe Ala Leu Lys Phe Leu Asp 60
Gln Ser Phe Val Pro Ile Thr
Asn Ser Leu Thr His Glu Leu Gln 75
Glu Lys Pro Ser Lys Trp Thr His 50
Phe Asn Arg Thr Ala Phe Leu
Gln Arg Gln Glu Ile Leu Gln 90
His Val Asp Val Ile Lys Asn Phe 105
Ser Leu Thr Lys Ser Ser Val Tyr
Arg Ile Gly Gln Leu Met His 120
Asp Tyr Ser Ser His Lys Tyr Phe 135
Val Phe Ser Ile Ser Asn Asn
Arg Ser Leu Leu Pro Asp Val Tyr 150
Ser Pro Ile Met Asn Lys Arg
Asn Val Cys Ala Val Val Gly 165
Asn Ser Gly Ile Leu Thr Gly Ser
Gln Cys Gly Gln Glu Ile Asp Cys
Lys Ser Asp Phe Val Ser Arg 180
Asn Phe Ala Pro Thr Glu Ala Lys 195
Phe His Lys Asp Val Gly Arg
Thr Asn Leu Thr Thr Phe Asn Tyr 210
Pro Ser Ile Leu Glu Lys Gln
Asn Asn Leu Leu Thr Ile Gln Ser 225
Asp Arg Asn Asn Phe Phe Leu Cys
Leu Lys Lys Leu Asp Gly Ala Phe
Ile Leu Trp Ile Pro Ala Phe Phe

Phe His Thr Ser Ala Thr Val 240
Thr Arg Thr Leu Val Asp Phe Phe
Val Glu His Arg Gly Gln Leu 255
Lys Val Gln Leu Ala Trp Pro Gly
Asn Ile Met Gln His Val Asn 270
Arg Tyr Trp Lys Asn Lys His Leu
Ser Pro Lys Arg Leu Ser Thr 285
Gly Ile Leu Met Tyr Thr Leu Ala
Ser Ala Ile Cys Glu Glu Ile 300
His Leu Tyr Gly Phe Trp Pro Phe
Gly Phe Asp Pro Asn Thr Arg 315
Glu Asp Leu Pro Tyr His Tyr Tyr
Asp Lys Lys Gly Thr Lys Phe 330
Thr Thr Lys Trp Gln Glu Ser His
Gln Leu Pro Ala Glu Phe Gln 345
Leu Leu Tyr Arg Met His Gly Glu
Gly Leu Thr Lys Leu Thr Leu 360
Ser His Cys Ala (364)  (SEQ ID. NO. 1)

2. An enzymatically active domain of the Siaα2,3Galβ1,4GlcNAcα2,8-sialyltransferase according to claim 1 capable of catalyzing Sia α2,3Galβ1,4GlcNAcα2,8-sialyltransfer.

3. The enzymatically active domain according to claim 2 characterized by the polypeptide sequence of from amino acid No.26 to 364 of the sequence (SEQ ID No: 3).

4. A polypeptide comprising the enzymatically active domain according to claim 2.

5. An extracellularly releasable protein comprising the enzymatically active domein according to claim 2.

6. An extracellularly releasable protein comprising the enzymatically active domain according to claim 3.

* * * * *

UNITED STATES PATENT AND TRADEMARK OFFICE
CERTIFICATE OF CORRECTION

PATENT NO.   : 5,798,244
DATED        : August 25, 1998
INVENTOR(S)  : Shuichi TSUJI et al.

It is certified that error appears in the above-identified patent and that said Letters Patent is hereby corrected as shown below:

At column 24, line 58 (claim 3, line 1) of the printed patent, change "domainin" to ---domain---.

At column 24, line 63 (claim 5, line 2) of the printed patent, change "domein" to ---domain---.

At column 24, line 63 (claim 5, line 2) of the printed patent, after "2" insert ---operably linked to a signal peptide---.

At column 24, line 65 of the printed patent, after "3" insert ---operably linked to a signal peptide---.

Signed and Sealed this

Third Day of April, 2001

Attest:

NICHOLAS P. GODICI

Attesting Officer

Acting Director of the United States Patent and Trademark Office

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 364 amino acids
( B ) TYPE: amino acid
( C ) STRANDEDNESS: Not Relevant
( D ) TOPOLOGY: linear ( x i ) SEQUENCE DESCRIPTION: SEQ ID NO:1:

```
Met Leu Ser Val Ala Leu Leu Ile Leu Ser Leu Ile Ser Tyr Val
1               5                   10                  15

Ser Leu Lys Lys Glu Asn Ile Phe Thr Thr Pro Lys Tyr Ala Ser
                20                  25                  30

Pro Gly Ala Pro Arg Met Tyr Met Phe His Ala Gly Phe Arg Ser
                35                  40                  45

Gln Phe Ala Leu Lys Phe Leu Asp Gln Ser Phe Val Pro Ile Thr
                50                  55                  60

Asn Ser Leu Thr His Glu Leu Gln Glu Lys Pro Ser Lys Trp Thr
                65                  70                  75

Phe Asn Arg Thr Ala Phe Leu His Gln Arg Gln Glu Ile Leu Gln
                80                  85                  90

His Val Asp Val Ile Lys Asn Phe Ser Leu Thr Lys Ser Ser Val
                95                  100                 105

Arg Ile Gly Gln Leu Met His Tyr Asp Tyr Ser Ser His Lys Tyr
                110                 115                 120

Val Phe Ser Ile Ser Asn Asn Phe Arg Ser Leu Leu Pro Asp Val
                125                 130                 135

Ser Pro Ile Met Asn Lys Arg Tyr Asn Val Cys Ala Val Val Gly
                140                 145                 150

Asn Ser Gly Ile Leu Thr Gly Ser Gln Cys Gly Gln Glu Ile Asp
                155                 160                 165

Lys Ser Asp Phe Val Ser Arg Cys Asn Phe Ala Pro Thr Glu Ala
```

|     |     |     |     |     |     |     |     | 170 |     |     |     |     | 175 |     |     |     |     | 180 |
| --- | --- | --- | --- | --- | --- | --- | --- | --- | --- | --- | --- | --- | --- | --- | --- | --- | --- | --- |
| Phe | His | Lys | Asp | Val | Gly | Arg | Lys | Thr | Asn | Leu | Thr | Thr | Phe | Asn |
|     |     |     |     | 185 |     |     |     |     | 190 |     |     |     |     | 195 |
| Pro | Ser | Ile | Leu | Glu | Lys | Tyr | Tyr | Asn | Asn | Leu | Leu | Thr | Ile | Gln |
|     |     |     |     | 200 |     |     |     |     | 205 |     |     |     |     | 210 |
| Asp | Arg | Asn | Asn | Phe | Phe | Leu | Ser | Leu | Lys | Lys | Leu | Asp | Gly | Ala |
|     |     |     |     | 215 |     |     |     |     | 220 |     |     |     |     | 225 |
| Ile | Leu | Trp | Ile | Pro | Ala | Phe | Phe | Phe | His | Thr | Ser | Ala | Thr | Val |
|     |     |     |     | 230 |     |     |     |     | 235 |     |     |     |     | 240 |
| Thr | Arg | Thr | Leu | Val | Asp | Phe | Phe | Val | Glu | His | Arg | Gly | Gln | Leu |
|     |     |     |     | 245 |     |     |     |     | 250 |     |     |     |     | 255 |
| Lys | Val | Gln | Leu | Ala | Trp | Pro | Gly | Asn | Ile | Met | Gln | His | Val | Asn |
|     |     |     |     | 260 |     |     |     |     | 265 |     |     |     |     | 270 |
| Arg | Tyr | Trp | Lys | Asn | Lys | His | Leu | Ser | Pro | Lys | Arg | Leu | Ser | Thr |
|     |     |     |     | 275 |     |     |     |     | 280 |     |     |     |     | 285 |
| Gly | Ile | Leu | Met | Tyr | Thr | Leu | Ala | Ser | Ala | Ile | Cys | Glu | Glu | Ile |
|     |     |     |     | 290 |     |     |     |     | 295 |     |     |     |     | 300 |
| His | Leu | Tyr | Gly | Phe | Trp | Pro | Phe | Gly | Phe | Asp | Pro | Asn | Thr | Arg |
|     |     |     |     | 305 |     |     |     |     | 310 |     |     |     |     | 315 |
| Glu | Asp | Leu | Pro | Tyr | His | Tyr | Tyr | Asp | Lys | Lys | Gly | Thr | Lys | Phe |
|     |     |     |     | 320 |     |     |     |     | 325 |     |     |     |     | 330 |
| Thr | Thr | Lys | Trp | Gln | Glu | Ser | His | Gln | Leu | Pro | Ala | Glu | Phe | Gln |
|     |     |     |     | 335 |     |     |     |     | 340 |     |     |     |     | 345 |
| Leu | Leu | Tyr | Arg | Met | His | Gly | Glu | Gly | Leu | Thr | Lys | Leu | Thr | Leu |
|     |     |     |     | 350 |     |     |     |     | 355 |     |     |     |     | 360 |
| Ser | His | Cys | Ala |
|     |     |     | 364 |

(2) INFORMATION FOR SEQ ID NO:2:

(i) SEQUENCE CHARACTERISTICS:
        (A) LENGTH: 1660 bases
        (B) TYPE: nucleic acid
        (C) STRANDEDNESS: Not Relevant
        (D) TOPOLOGY: linear (xi) SEQUENCE DESCRIPTION: SEQ ID NO:2:

```
                                          GG CACGAGGCCA GCAGGCTGCT         22
GGCGCTCAAT GGACCGATTT CCCCGGTTTC CCTGAACCCA GCCTAGCCCG                     72
GGATGAGAAA TTGCAAAATG GCCCGAGTCG CCAGTGTGCT AGGGCTGGTC                    122

ATG CTC AGC GTG GCC CTG CTG ATT TTA TCG CTT ATC AGC TAC GTG              167
Met Leu Ser Val Ala Leu Leu Ile Leu Ser Leu Ile Ser Tyr Val
 1               5                  10                 15

TCT CTG AAA AAG GAG AAC ATC TTC ACC ACT CCC AAG TAC GCC AGC              212
Ser Leu Lys Lys Glu Asn Ile Phe Thr Thr Pro Lys Tyr Ala Ser
                20                  25                 30

CCG GGG GCG CCC CGA ATG TAC ATG TTC CAC GCG GGA TTC CGG TCA              257
Pro Gly Ala Pro Arg Met Tyr Met Phe His Ala Gly Phe Arg Ser
                35                  40                 45

CAG TTT GCA CTG AAG TTT CTA GAC CAG TCA TTT GTG CCC ATT ACG              302
Gln Phe Ala Leu Lys Phe Leu Asp Gln Ser Phe Val Pro Ile Thr
                50                  55                 60

AAT TCT CTC ACC CAT GAA CTC CAA GAG AAA CCT TCT AAA TGG ACA              347
Asn Ser Leu Thr His Glu Leu Gln Glu Lys Pro Ser Lys Trp Thr
                65                  70                 75

TTT AAT CGG ACA GCG TTT TTA CAT CAA AGG CAA GAA ATT CTT CAG              392
Phe Asn Arg Thr Ala Phe Leu His Gln Arg Gln Glu Ile Leu Gln
```

```
                    80                          85                          90
CAT GTC GAT GTA ATA AAA AAT TTT TCT TTG ACC AAG AGT AGT GTT       437
His Val Asp Val Ile Lys Asn Phe Ser Leu Thr Lys Ser Ser Val
                 95                      100                     105

CGG ATT GGA CAA CTA ATG CAT TAT GAT TAT TCC AGC CAT AAA TAT       482
Arg Ile Gly Gln Leu Met His Tyr Asp Tyr Ser Ser His Lys Tyr
                110                      115                     120

GTC TTC TCG ATT AGC AAT AAC TTC CGG TCC CTG CTC CCA GAT GTG       527
Val Phe Ser Ile Ser Asn Asn Phe Arg Ser Leu Leu Pro Asp Val
                125                      130                     135

TCG CCC ATT ATG AAT AAG CGT TAT AAT GTT TGT GCT GTG GTT GGA       572
Ser Pro Ile Met Asn Lys Arg Tyr Asn Val Cys Ala Val Val Gly
                140                      145                     150

AAC AGT GGA ATC TTG ACA GGG AGT CAG TGT GGA CAA GAA ATA GAT       617
Asn Ser Gly Ile Leu Thr Gly Ser Gln Cys Gly Gln Glu Ile Asp
                155                      160                     165

AAA TCA GAT TTT GTT TCT CGA TGC AAT TTT GCC CCG ACA GAG GCT       662
Lys Ser Asp Phe Val Ser Arg Cys Asn Phe Ala Pro Thr Glu Ala
                170                      175                     180

TTC CAC AAA GAT GTT GGA AGG AAA ACC AAC CTC ACA ACC TTC AAT       707
Phe His Lys Asp Val Gly Arg Lys Thr Asn Leu Thr Thr Phe Asn
                185                      190                     195

CCG AGC ATC TTA GAG AAA TAT TAC AAC AAT CTT TTA ACC ATT CAG       752
Pro Ser Ile Leu Glu Lys Tyr Tyr Asn Asn Leu Leu Thr Ile Gln
                200                      205                     210

GAC CGT AAC AAC TTC TTC CTC AGT TTA AAA AAG CTT GAT GGG GCC       797
Asp Arg Asn Asn Phe Phe Leu Ser Leu Lys Lys Leu Asp Gly Ala
                215                      220                     225

ATA CTT TGG ATC CCT GCA TTT TTC TTC CAC ACT TCT GCA ACT GTA       842
Ile Leu Trp Ile Pro Ala Phe Phe Phe His Thr Ser Ala Thr Val
                230                      235                     240

ACG AGA ACG CTA GTG GAT TTT TTT GTT GAG CAC AGA GGT CAG TTA       887
Thr Arg Thr Leu Val Asp Phe Phe Val Glu His Arg Gly Gln Leu
                245                      250                     255

AAG GTC CAG TTG GCT TGG CCT GGA AAT ATC ATG CAA CAT GTC AAC       932
Lys Val Gln Leu Ala Trp Pro Gly Asn Ile Met Gln His Val Asn
                260                      265                     270

AGG TAC TGG AAA AAC AAA CAC CTG TCA CCC AAA CGA CTG AGC ACA       977
Arg Tyr Trp Lys Asn Lys His Leu Ser Pro Lys Arg Leu Ser Thr
                275                      280                     285

GGT ATC CTA ATG TAT ACT CTT GCA TCT GCA ATA TGT GAA GAG ATC      1022
Gly Ile Leu Met Tyr Thr Leu Ala Ser Ala Ile Cys Glu Glu Ile
                290                      295                     300

CAC TTG TAC GGT TTC TGG CCC TTT GGA TTT GAC CCC AAC ACC AGG      1067
His Leu Tyr Gly Phe Trp Pro Phe Gly Phe Asp Pro Asn Thr Arg
                305                      310                     315

GAG GAT CTG CCC TAC CAC TAC TAT GAC AAA AAA GGA ACC AAA TTT      1112
Glu Asp Leu Pro Tyr His Tyr Tyr Asp Lys Lys Gly Thr Lys Phe
                320                      325                     330

ACC ACC AAG TGG CAG GAG TCT CAC CAG CTG CCT GCT GAG TTT CAG      1157
Thr Thr Lys Trp Gln Glu Ser His Gln Leu Pro Ala Glu Phe Gln
                335                      340                     345

CTG CTC TAT CGA ATG CAT GGG GAA GGG CTC ACG AAG CTC ACT CTG      1202
Leu Leu Tyr Arg Met His Gly Glu Gly Leu Thr Lys Leu Thr Leu
                350                      355                     360

TCA CAC TGT GCC TAA                                              1217
Ser His Cys Ala ---

GAACTCCAAA TGGAAAGTGC CAAACGGCTG ATTAAAAAGT GCCCTCACCC           1267

CCAAACCAAA TTGAATAGTC TCCAGAACAG AACCCATAGA CAATCTGGCA           1317
```

|  |  |  |  |  |
|---|---|---|---|---|
| AAGCCTGTCT | GCCACTTACA | AGGAAAGACG | CCTTCTCTTC | CTCTTTTGCA | 1367 |
| CTGCTCTTTG | AATGGTCTTA | ACAAACTTAG | GACAGGTGCA | TTGAAGCCGT | 1417 |
| GTGATTTAGA | CTTGATTGGG | AAAAGGTTAT | ATTGCATTTG | GAAGTATGCT | 1467 |
| GCACAGAGAA | TAGCTTGAAA | TAGTTCTAAG | TTTGTATTTT | AATAATAAAC | 1517 |
| CGACTCCCAT | GTGAATGAGG | AATGTGACTG | TCATCTCCTC | CTCTCTACTT | 1567 |
| TGATATAGTC | CTCACAACCA | GGGAGCTCTG | GCCAGCTCCA | GCAGGATCTC | 1617 |
| TTTAGCCAAG | GGGATCAGAA | TCTTCAAAAA | AAAAAAAAAA | AAA | 1660 |

(2) INFORMATION FOR SEQ ID NO:3:

(i) SEQUENCE CHARACTERISTICS:
        (A) LENGTH: 339 amino acids
        (B) TYPE: amino acid
        (C) STRANDEDNESS: Not Relevant
        (D) TOPOLOGY: linear (xi) SEQUENCE DESCRIPTION: SEQ ID NO:3:

```
Pro Lys Tyr Ala Ser Pro Gly Ala Pro Arg Met Tyr Met Phe His
 1               5                  10                  15

Ala Gly Phe Arg Ser Gln Phe Ala Leu Lys Phe Leu Asp Gln Ser
                20                  25                  30

Phe Val Pro Ile Thr Asn Ser Leu Thr His Glu Leu Gln Glu Lys
                35                  40                  45

Pro Ser Lys Trp Thr Phe Asn Arg Thr Ala Phe Leu His Gln Arg
                50                  55                  60

Gln Glu Ile Leu Gln His Val Asp Val Ile Lys Asn Phe Ser Leu
                65                  70                  75

Thr Lys Ser Ser Val Arg Ile Gly Gln Leu Met His Tyr Asp Tyr
                80                  85                  90

Ser Ser His Lys Tyr Val Phe Ser Ile Ser Asn Asn Phe Arg Ser
                95                 100                 105

Leu Leu Pro Asp Val Ser Pro Ile Met Asn Lys Arg Tyr Asn Val
               110                 115                 120

Cys Ala Val Val Gly Asn Ser Gly Ile Leu Thr Gly Ser Gln Cys
               125                 130                 135

Gly Gln Glu Ile Asp Lys Ser Asp Phe Val Ser Arg Cys Asn Phe
               140                 145                 150

Ala Pro Thr Glu Ala Phe His Lys Asp Val Gly Arg Lys Thr Asn
               155                 160                 165

Leu Thr Thr Phe Asn Pro Ser Ile Leu Glu Lys Tyr Tyr Asn Asn
               170                 175                 180

Leu Leu Thr Ile Gln Asp Arg Asn Asn Phe Phe Leu Ser Leu Lys
               185                 190                 195

Lys Leu Asp Gly Ala Ile Leu Trp Ile Pro Ala Phe Phe Phe His
               200                 205                 210

Thr Ser Ala Thr Val Thr Arg Thr Leu Val Asp Phe Phe Val Glu
               215                 220                 225

His Arg Gly Gln Leu Lys Val Gln Leu Ala Trp Pro Gly Asn Ile
               230                 235                 240

Met Gln His Val Asn Arg Tyr Trp Lys Asn Lys His Leu Ser Pro
               245                 250                 255

Lys Arg Leu Ser Thr Gly Ile Leu Met Tyr Thr Leu Ala Ser Ala
               260                 265                 270
```

```
Ile Cys Glu Glu Ile His Leu Tyr Gly Phe Trp Pro Phe Gly Phe
            275                 280                 285

Asp Pro Asn Thr Arg Glu Asp Leu Pro Tyr His Tyr Tyr Asp Lys
            290                 295                 300

Lys Gly Thr Lys Phe Thr Thr Lys Trp Gln Glu Ser His Gln Leu
            305                 310                 315

Pro Ala Glu Phe Gln Leu Leu Tyr Arg Met His Gly Glu Gly Leu
            320                 325                 330

Thr Lys Leu Thr Leu Ser His Cys Ala
            335             339
```

( 2 ) INFORMATION FOR SEQ ID NO:4:

( i ) SEQUENCE CHARACTERISTICS:
        ( A ) LENGTH: 1048 bases
        ( B ) TYPE: nucleic acid
        ( C ) STRANDEDNESS: Not Relevant
        ( D ) TOPOLOGY: linear ( x i ) SEQUENCE DESCRIPTION: SEQ ID NO:4:

```
                                                    CAT CTTCTCGAGT      13

CCC AAG TAC GCC AGC CCG GGG GCG CCC CGA ATG TAC ATG TTC CAC             58
Pro Lys Tyr Ala Ser Pro Gly Ala Pro Arg Met Tyr Met Phe His
1               5                   10                  15

GCG GGA TTC CGG TCA CAG TTT GCA CTG AAG TTT CTA GAC CAG TCA            103
Ala Gly Phe Arg Ser Gln Phe Ala Leu Lys Phe Leu Asp Gln Ser
                20                  25                  30

TTT GTG CCC ATT ACG AAT TCT CTC ACC CAT GAA CTC CAA GAG AAA            148
Phe Val Pro Ile Thr Asn Ser Leu Thr His Glu Leu Gln Glu Lys
                35                  40                  45

CCT TCT AAA TGG ACA TTT AAT CGG ACA GCG TTT TTA CAT CAA AGG            193
Pro Ser Lys Trp Thr Phe Asn Arg Thr Ala Phe Leu His Gln Arg
                50                  55                  60

CAA GAA ATT CTT CAG CAT GTC GAT GTA ATA AAA AAT TTT TCT TTG            238
Gln Glu Ile Leu Gln His Val Asp Val Ile Lys Asn Phe Ser Leu
                65                  70                  75

ACC AAG AGT AGT GTT CGG ATT GGA CAA CTA ATG CAT TAT GAT TAT            283
Thr Lys Ser Ser Val Arg Ile Gly Gln Leu Met His Tyr Asp Tyr
                80                  85                  90

TCC AGC CAT AAA TAT GTC TTC TCG ATT AGC AAT AAC TTC CGG TCC            328
Ser Ser His Lys Tyr Val Phe Ser Ile Ser Asn Asn Phe Arg Ser
                95                  100                 105

CTG CTC CCA GAT GTG TCG CCC ATT ATG AAT AAG CGT TAT AAT GTT            373
Leu Leu Pro Asp Val Ser Pro Ile Met Asn Lys Arg Tyr Asn Val
                110                 115                 120

TGT GCT GTG GTT GGA AAC AGT GGA ATC TTG ACA GGG AGT CAG TGT            418
Cys Ala Val Val Gly Asn Ser Gly Ile Leu Thr Gly Ser Gln Cys
                125                 130                 135

GGA CAA GAA ATA GAT AAA TCA GAT TTT GTT TCT CGA TGC AAT TTT            463
Gly Gln Glu Ile Asp Lys Ser Asp Phe Val Ser Arg Cys Asn Phe
                140                 145                 150

GCC CCG ACA GAG GCT TTC CAC AAA GAT GTT GGA AGG AAA ACC AAC            508
Ala Pro Thr Glu Ala Phe His Lys Asp Val Gly Arg Lys Thr Asn
                155                 160                 165

CTC ACA ACC TTC AAT CCG AGC ATC TTA GAG AAA TAT TAC AAC AAT            553
Leu Thr Thr Phe Asn Pro Ser Ile Leu Glu Lys Tyr Tyr Asn Asn
                170                 175                 180

CTT TTA ACC ATT CAG GAC CGT AAC AAC TTC TTC CTC AGT TTA AAA            598
Leu Leu Thr Ile Gln Asp Arg Asn Asn Phe Phe Leu Ser Leu Lys
                185                 190                 195
```

-continued

| | | | | | | | | | | | | | | | |
|---|---|---|---|---|---|---|---|---|---|---|---|---|---|---|---|
| AAG | CTT | GAT | GGG | GCC | ATA | CTT | TGG | ATC | CCT | GCA | TTT | TTC | TTC | CAC | 643 |
| Lys | Leu | Asp | Gly | Ala | Ile | Leu | Trp | Ile | Pro | Ala | Phe | Phe | Phe | His | |
| | | | | 200 | | | | | 205 | | | | | 210 | |
| ACT | TCT | GCA | ACT | GTA | ACG | AGA | ACG | CTA | GTG | GAT | TTT | TTT | GTT | GAG | 688 |
| Thr | Ser | Ala | Thr | Val | Thr | Arg | Thr | Leu | Val | Asp | Phe | Phe | Val | Glu | |
| | | | | 215 | | | | | 220 | | | | | 225 | |
| CAC | AGA | GGT | CAG | TTA | AAG | GTC | CAG | TTG | GCT | TGG | CCT | GGA | AAT | ATC | 733 |
| His | Arg | Gly | Gln | Leu | Lys | Val | Gln | Leu | Ala | Trp | Pro | Gly | Asn | Ile | |
| | | | | 230 | | | | | 235 | | | | | 240 | |
| ATG | CAA | CAT | GTC | AAC | AGG | TAC | TGG | AAA | AAC | AAA | CAC | CTG | TCA | CCC | 778 |
| Met | Gln | His | Val | Asn | Arg | Tyr | Trp | Lys | Asn | Lys | His | Leu | Ser | Pro | |
| | | | | 245 | | | | | 250 | | | | | 255 | |
| AAA | CGA | CTG | AGC | ACA | GGT | ATC | CTA | ATG | TAT | ACT | CTT | GCA | TCT | GCA | 823 |
| Lys | Arg | Leu | Ser | Thr | Gly | Ile | Leu | Met | Tyr | Thr | Leu | Ala | Ser | Ala | |
| | | | | 260 | | | | | 265 | | | | | 270 | |
| ATA | TGT | GAA | GAG | ATC | CAC | TTG | TAC | GGT | TTC | TGG | CCC | TTT | GGA | TTT | 868 |
| Ile | Cys | Glu | Glu | Ile | His | Leu | Tyr | Gly | Phe | Trp | Pro | Phe | Gly | Phe | |
| | | | | 275 | | | | | 280 | | | | | 285 | |
| GAC | CCC | AAC | ACC | AGG | GAG | GAT | CTG | CCC | TAC | CAC | TAC | TAT | GAC | AAA | 913 |
| Asp | Pro | Asn | Thr | Arg | Glu | Asp | Leu | Pro | Tyr | His | Tyr | Tyr | Asp | Lys | |
| | | | | 290 | | | | | 295 | | | | | 300 | |
| AAA | GGA | ACC | AAA | TTT | ACC | ACC | AAG | TGG | CAG | GAG | TCT | CAC | CAG | CTG | 958 |
| Lys | Gly | Thr | Lys | Phe | Thr | Thr | Lys | Trp | Gln | Glu | Ser | His | Gln | Leu | |
| | | | | 305 | | | | | 310 | | | | | 315 | |
| CCT | GCT | GAG | TTT | CAG | CTG | CTC | TAT | CGA | ATG | CAT | GGG | GAA | GGG | CTC | 1003 |
| Pro | Ala | Glu | Phe | Gln | Leu | Leu | Tyr | Arg | Met | His | Gly | Glu | Gly | Leu | |
| | | | | 320 | | | | | 325 | | | | | 330 | |
| ACG | AAG | CTC | ACT | CTG | TCA | CAC | TGT | GCC | TAA | | | | | | 1033 |
| Thr | Lys | Leu | Thr | Leu | Ser | His | Cys | Ala | --- | | | | | | |
| | | | | 335 | | | | 339 | | | | | | | |

GAACTCGAGA TGGAA  1048